(12) United States Patent
Godin et al.

(10) Patent No.: US 6,444,230 B1
(45) Date of Patent: *Sep. 3, 2002

(54) SYNERGISTIC COMPOSITION OF PERACETIC ACID AND AMINE OXIDE

(75) Inventors: Catherine Hamon Godin, Chatillon (FR); Yves Gouges, Paris (FR); Daniel Le Rouzic, Ermont (FR)

(73) Assignees: Chemoxal SA, Paris Cedex (FR); Societe d'Exploitation de Produits pour les Industries Chimiques Seppic, Paris Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/715,263

(22) Filed: Nov. 20, 2000

Related U.S. Application Data

(62) Division of application No. 09/065,563, filed on Apr. 24, 1998, now Pat. No. 6,168,808.

(30) Foreign Application Priority Data

Apr. 24, 1997 (FR) .............................. 97 05052
Dec. 24, 1997 (FR) .............................. 97 16490

(51) Int. Cl.$^7$ ................. A01N 59/00; A01N 25/00; A01N 31/00; A01N 33/00; A01N 37/00
(52) U.S. Cl. ............... 424/616; 424/126; 514/183; 514/211; 514/212.01; 514/218; 514/277; 514/430; 514/431; 514/449; 514/450; 514/557; 514/579; 514/644; 514/663; 514/665; 514/667; 514/672; 514/673; 514/674; 514/715; 514/717; 514/718; 514/719; 514/720; 514/722; 514/723; 514/727; 514/772; 514/788; 514/970; 514/975
(58) Field of Search ................. 424/126, 616; 514/183, 211, 212, 218, 277, 430, 431, 449, 450, 557, 579, 644, 663, 665, 667, 672, 673, 674, 715, 717, 718, 719, 720, 722, 723, 727, 772, 772.1, 788, 970, 975, 212.01

(56) References Cited

U.S. PATENT DOCUMENTS

| 4,518,585 A | * | 5/1985 | Greene et al. ............... 424/616 |
| 5,489,706 A | * | 2/1996 | Revell ............................ 562/3 |
| 5,545,343 A | * | 8/1996 | Brougham et al. ......... 514/557 |
| 5,545,374 A | * | 8/1996 | French et al. .................. 422/28 |
| 5,645,648 A | * | 7/1997 | Laut et al. ...................... 134/2 |
| 5,851,483 A | * | 12/1998 | Nicolle et al. ................ 422/28 |

FOREIGN PATENT DOCUMENTS

| GB | 2 255 507 A | * 11/1992 |
| WO | WO 9619558 | 6/1996 |
| WO | WO 9619559 | 6/1996 |

* cited by examiner

Primary Examiner—Jose' G. Dees
Assistant Examiner—Frank Choi
(74) Attorney, Agent, or Firm—Young & Thompson

(57) ABSTRACT

Composition in the form of an aqueous solution, useful for disinfecting hard surfaces comprises:

a) from 0.0005% to 20% by weight of peracetic acid,
b) from 0.001% to 45% by weight of acetic acid,
c) from 0.001% to 35% by weight of hydrogen peroxide,
d) from 0.0001% to 2% by weight of at least one compound of formula (I)

$$(R_1)(R_2)(R_3)N \rightarrow O \qquad (I)$$

e) if desired, up to 2.5% by weight of at least one nonionic surfactant, and wherein
f) the weight ratio between the compound of formula (I) and the peracetic acid is less than or equal to 1, and in that
g) the weight ratio between the nonionic surfactant and the peracetic acid is less than or equal to 0.2.

12 Claims, No Drawings

SYNERGISTIC COMPOSITION OF PERACETIC ACID AND AMINE OXIDE

This application is a division of Application Ser. No. 09/065,563, filed on Apr. 24, 1998, now U.S. Pat. No. 6,168,808, the entire contents of which are hereby incorporated by reference.

FILED OF THE INVENTION

The invention relates to novel disinfectant compositions containing peracetic acid.

BACKGROUND OF THE INVENTION

Such solutions are nowadays widely used in many industrial sectors. The increasing interest in peracetic acid lies in its wide range of biocidal activity, in particular with respect to bacteria, algae, yeasts, moulds, fungi and viruses. However, dilute solutions of peracetic acid are of insufficient wetting performance on the surfaces commonly treated, for example in the medical and hospital fields, in the agrifood, pharmaceutical, cosmetics and microelectronics industries, bioindustries, collectives and, more generally, in any activity for which controlling the population of microorganisms is required. The surfaces to be treated are very diverse; mention may be made, for example, of premises, equipment, apparatus, tools and utensils, containers such as tanks, package wrapping and pipes. It has thus been sought to lower the surface tension of these disinfectant solutions by adding surfactants. Among the documents of the prior art, mention may be made in particular of those which describe compositions containing a peracid and a nonionic surfactant, for instance the international patent applications published under the numbers WO 88/08667, WO 93/10088 and WO 94/14321 or European patent applications EP 193,416 and EP 596,493.

However, none of the peracetic acid-based disinfectant solutions described in that prior art has the set of properties required in order to be commercially acceptable; these properties are as follows: the solution should contain both peracetic acid and the surfactant, it should be stable over time, it should have a high wetting power and a low foaming power, it should be easily rinsable, be clear in appearance, it should contain minimum amounts of chemical products, while at the same time being sufficiently active on microorganisms after dilution, and, lastly, the surfactant(s) used should be compatible with peracetic acid. Furthermore, when it is a matter of disinfecting and sterilizing equipment, it is essential for the disinfectant solution to have improved fungicidal activity. This requirement is unavoidable where medico-surgical activities are concerned such as, for example, endoscopy, both interventional and exploratory, which is in full development. Indeed, it may thus be feared that a multiplication of endoscopic interventions might be accompanied by a multiplication of post-endoscopic infections. For this reason, the disinfection procedures to be applied to reusable medical equipment are of great importance in protecting both patients and the care staff against the risks of infection.

Among reusable medical equipment, flexible endoscopes are particularly expensive. Given the limited number of these items of equipment in hospitals, their reuse is increasingly frequent and, consequently, the delay between two interventions is increasingly short. For this reason, these practices give rise to new disinfection procedures characterized mainly by their simplicity, their speed and their reduced cost.

However, the use of peracetic acid alone, as fungicidal agent, requires high effective doses. Usually, the solutions lack remanence. This has given rise to interest in reinforcing them by adding a fungicidal agent in order to increase the longevity of disinfectant baths and to reduce the effective doses to be used.

Antimicrobial active principles have different modes of action. In general, they act either on the intracellular constituents (enzymes, mitochondria, etc.) or on the extracellular constituents (cytoplasmic membrane and cell wall). Compounds which act inside the cell must, in order to reach their target, cross the barrier formed by the cytoplasmic membrane, and hence the interest in acting on the latter. Quaternary ammoniums are recognized as having excellent antimicrobial power, due to the fact that they are positively charged surfactants. Since the cell membrane is negatively charged, they can be absorbed thereon rapidly and become bound, which will disrupt the cytoplasmic membrane, modify the cell permeability and precipitate the cell constituents, leading to rapid death of the cell even at low doses. Positively charged compounds of high molecular weight thus prove to be worthy of interest (betaines, phosphonium salts, zwitterions, quaternary ammoniums, etc.). Many references exist on the industrial exploitation of quaternary ammoniums. Amine oxides are advantageous compounds since, when placed in acidic solution, they become cationic.

Amine oxides have been the subject of many studies. They are generally biodegradable and prove to be very effective constituents in detergents and shampoos, but also in disinfection. As a reference, mention may be made of the review by S. H. Shapiro, pages 32 to 50, published in the supplement to the 2nd edition of Kirk Othmer's Encyclopaedia of Chemical Technology.

Amine oxides have, to date, been used only as co-surfactants in thickened compositions. Mention may be made for example, in this respect, of the international patent applications published under the numbers WO 96/19558, WO 96/19559 and WO 96/17044 and U.S. Pat. No. 5,078, 896.

SUMMARY OF THE INVENTION

The Applicant has now found, unexpectedly, that amine oxides act in synergy with peracetic acid, at concentrations in solution which do not lead to any appreciable thickening of the solution.

The subject of the present invention is thus a composition in the form of an aqueous solution, characterized in that it comprises:

a) from 0.0005% to 20% by weight of peracetic acid,
b) from 0.001% to 45% by weight of acetic acid,
c) from 0.001% to 35% by weight of hydrogen peroxide,
d) from 0.0001% to 2% by weight of at least one compound of formula (I)

$$(R^1)(R_2)(R_3)N \to O \tag{I}$$

in which, either $R_1$ represents a linear or branched, cyclic or acyclic radical containing from 1 to 40 carbon atoms and optionally from 1 to 6 hetero atoms chosen from oxygen, sulphur and nitrogen, and $R_2$ and $R_3$, which may be identical or different, represent a linear or branched alkyl radical containing from 1 to 4 carbon atoms or a linear or branched hydroxyalkyl radical containing from 1 to 4 carbon atoms; or $R^1$ and $R_2$ represent, together with the nitrogen atom to which they are attached, a saturated or unsaturated, substituted or unsubstituted heterocycle containing from 5 to 8 carbon atoms and from 1 to 4 hetero atoms chosen from oxygen, nitrogen and sulphur, and $R_3$ represents a linear or branched alkyl radical containing from 1 to 4 carbon atoms or a linear or branched hydroxyalkyl radical containing from 1 to 4 carbon atoms, e) if desired, up to 2.5% by weight of at least one nonionic surfactant, and characterized in that f) the weight ratio between the compound of formula (I) and the peracetic acid is less than or equal to 1, and in that g) the weight ratio between the nonionic surfactant and the peracetic acid is less than or equal to 0.2, provided that the nonionic surfactant which is optionally comprised within said composition is not a compound having the general formula (III):

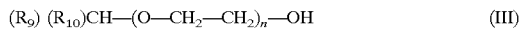

$$(R_9)(R_{10})CH-(O-CH_2-CH_2)_n-OH \quad (III)$$

in which $R_9$ and $R_{10}$ are each either hydrogen or linear or branched alkyl such that $R_9$ plus $R_{10}$ has a total of from 7 to 22 carbon atoms, and n is selected in the range of 1 to 15, such that the number ratio of carbon atoms in $R_9$ plus $R_{10}$: n is greater than or equal to 3:1 and provided that the non-ionic surfactant is not a dinonyl phenolethoxylate of EO from 4 to 8.

When $R_1$ represents an acyclic radical, it is in particular a linear or branched alkyl radical; this radical can be unsubstituted, monosubstituted or polysubstituted; when this radical is substituted, the substituent(s) is (are) chosen, independently of each other, from hydroxyl, alkyloxy, alkylthio, carboxyl and alkoxycarbonyl radicals, from halogen atoms or from cycloalkyl or phenyl radicals; when $R_1$ represents a cyclic radical, it is a mononuclear or polynuclear radical; this radical can be unsubstituted, monosubstituted or polysubstituted; when this radical is substituted, the substituent(s) is (are) chosen, independently of each other, from hydroxyl, alkyloxy, alkylthio, carboxyl and alkoxycarbonyl radicals, from halogen atoms or from cycloalkyl or phenyl radicals or alternatively from alkyl radicals; when $R_1$ represents a mononuclear radical, it is a phenyl or cycloalkyl radical; when $R_1$ represents a polynuclear radical, it concerns in particular saturated bicycles which are aromatic or contain an aromatic ring; when $R_1$ and $R_2$ represent, with the nitrogen atom to which they are attached, a heterocycle, it is a saturated or aromatic mononuclear radical or a saturated polynuclear radical which is aromatic or contains an aromatic ring; this mononuclear or polynuclear radical can be unsubstituted, monosubstituted or polysubstituted; when this radical is substituted, the substituent(s) is (are) chosen, independently of each other, from hydroxyl, alkyloxy, alkylthio, carboxyl and alkoxycarbonyl radicals, from halogen atoms or from cycloalkyl or phenyl radicals or alternatively from alkyl radicals.

By way of non-limiting example, mention may be made of the compounds of formula (I) as defined above, in which $R_1$ represents a methyl, ethyl, propyl, butyl, phenyl, tolyl, benzyl, octyl, nonyl, decyl, undecyl, dodecyl, tridecyl, tetradecyl, pentadecyl, hexadecyl, heptadecyl, octadecyl, imidazolinyl, morpholinyl, piperidyl, oxazolinyl, piperazinyl, pentyl, hexyl, heptyl, norbornyl, cyclopentyl, cyclohexyl, thiazolyl, oxazolyl, naphthyl, tetrahydronaphthyl, phenethyl, pyridyl, quinolyl, 1-carboxypyridyl,1-methoxycarbonylpyridyl or a 1-ethoxycarbonylpyridyl radical or the compounds of formula (I) in which $R_1$ and $R_2$ represent, with the atom to which they are attached, an imidazolinyl, morpholinyl, piperidyl, oxazolinyl, piperazinyl, pyridyl, quinolyl, 1-carboxypyridyl, 1-methoxycarbonylpyridyl, 1-ethoxycarbonylpyridyl, thiazolyl or an oxazolyl radical.

Such compounds of formula (I) can be prepared according to methods known to those skilled in the art from the corresponding amine, or are commercially available under the trade name Aromox® such as the compound Aromox® MCD-W.

The expression at least one compound of formula (I) is understood to refer to either a single compound of formula (I) or to a mixture of compounds of formula (I); in the latter case, it is clearly understood that the weight percentages indicated apply to the mixture as a whole.

The expression at least one nonionic surfactant is understood to denote one or more surfactants which are only sparingly or not at all ionized in aqueous solution. Mention may be made, for example, of alkoxylated fatty alcohols, alkoxylated fatty acids, alkoxylated alkylphenols, alkoxylated fatty amines and alkoxylated polypropylene glycols, it being possible for the hydroxyl functions of these compounds to be free or blocked.

By way of non-limiting example the non-ionic surfactant may be, Genapol® 2822, Genapol® 2908, Genapol® 2908D, Genapol® 2909, Tritone® DF12, Triton® DF16, Dowfax® 20B102, Akypo® RO90, Akypo® LF2, Akypo® LF4, Synperonic® LF RA 30, ou Simulsol® NW 900, these products all being commercially available and the Chemical composition of which being as follows:

| Name | Chemical Composition of the Surfactant |
| --- | --- |
| Genapol ® 2822 | mixture of alkoxylated alcohols in $C_{10}$, $C_{12}$, $C_{14}$, (5 EO, 4 PO) |
| Genapol ® 2908D | mixture of alkoxylated alcohols in $C_{11}$, $C_{13}$, $C_{15}$, (6 to 7 EO, 3 PO) |
| Genapol ® 2909 | mixture of alkoxylated alcohols in $C_{12}$ and $C_{14}$, (5 EO, 3 PO) |
| Simulsol ® NW 900 | mixture of alkoxylated alcohols (x EO, y PO) |
| Triton ® DF 12 | benzylic ether of alkoxylated alcohols in $C_8$, $C_{10}$, (2 EO, 5 PO) |
| Triton ® CF 10 | benzylic ether of alkoxylated alcohols $C_8$ (16 EO) |
| Akypo ® RO 90 | ethoxylated carboxylic ether in $C_{16}$, $C_{18}$ (9 EO) |
| Dowfax ® 20B102 | diphenylsulfonate surfactant from Dow Chemical |
| Triton ® DF16 | mixture of alkoxylated alcohols in $C_8$, $C_{10}$ (6 EO, 3 PO) |
| Akypo ® LF2 | ethoxylated carboxylic ether in $C_8$ (8 EO) |
| Akypo ® LF4 | ethoxylated carboxylic ether in $C_6$, $C_8$ (7 EO) |

The subject of a first variant of the invention is a composition as defined above which comprises, as nonionic surfactant, at least one compound of formula (II)

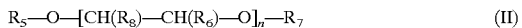

$$R_5-O-[CH(R_8)-CH(R_6)-O]_n-R_7 \quad (II)$$

in which $R_5$ represents a linear or branched, saturated or unsaturated aliphatic radical containing from 5 to 31 carbon atoms and preferably from 10 to 16 carbon atoms; $R_6$ represents a hydrogen atom, a methyl radical or an ethyl radical, $R_8$ represents a hydrogen atom, a methyl radical or an ethyl radical, it being understood that at least one of the two radicals $R_6$ or $R_8$ represents a hydrogen atom, $R_7$ represents a hydrogen atom or a linear or branched alkyl radical containing from 1 to 4 carbon atoms, or a benzyl radical, n represents a number between 1 and 50, and preferably n is less than 20 provided that the compound of formula (II) is not a compound of formula (III) as defined above.

The expression at least one compound of formula (II) is understood to refer either to a compound of formula (II) or to a mixture of compounds of formula (II); in the latter case, it is clearly understood that the weight percentages apply to the mixture as a whole.

In the definition of formula (II), the group [CH($R_8$)—CH($R_6$)—O]$_n$ means that it can be a chain composed solely of ethoxyl groups ($R_6$ and $R_8$=H), solely of propoxyl groups ($R_6$ or $R_8$=CH$_3$), solely of butoxyl groups ($R_6$ or $R_8$=CH$_2$—CH$_3$) or of a mixture of two types or of the three types of group.

In the latter case, the various fragments are distributed in a random or block manner.

The subject of the invention is, in particular, the composition as defined above in which, in formula (I), $R_1$ represents a linear or branched aliphatic radical containing from 8 to 18 carbon atoms and $R_2$ and $R_3$ each represent a methyl radical.

In a second preferred variant of the present invention, the composition as defined above comprises from 0.0001% to 2% by weight, and in particular from 0.0002% to 2% by weight, of at least one nonionic surfactant.

In a third preferred variant of the present invention, in formula (I), $R_1$ is chosen from octyl, decyl, dodecyl, tetradecyl and hexadecyl radicals.

As a compound of formula (I) which is suitable in the present invention, there are in particular cocodimethylamine oxide, myristamine oxide, dihydroxyethylcocoamine oxide, dimethylstearylamine oxide and dyethylstearylamine oxide.

In a fourth preferred variant of the present invention, in formula (II), $R_1$ represents a hydrogen atom.

In a fifth preferred variant of the present invention, in formula (II), either the group [CH($R_8$)—CH($R_6$)—O]$_n$ solely represents [CH$_2$—CH$_2$—O]$_n$ structural units or the group [CH($R_8$)—CH($R_6$)—O]$_n$ represents a chain consisting approximately of between 5 and 8 —(CH$_2$—CH$_2$—O)— structural units and approximately of between 1 and 5 —(CH$_2$—CH(CH$_3$)—O)— structural units, the structural units being distributed in the chain in a random or block manner.

As compounds of formula (II) which are suitable in the present invention, there are in particular Genapol® 2822, Genapol® 2908, Genapol® 2908D, Genapol® 2909, Triton® DF12, Dowfax® 20B102, Akypo® RO 90, Synperonic® LF RA 30 and Simulsol® NW 900, these products all being commercially available.

The aqueous solutions according to the invention can also contain standard compounds known to those skilled in the art, such as stabilizers; such compounds are, in general, present in the solution of peracetic acid and hydrogen peroxide used for the preparation of the compositions according to the invention; they are, for example, strong acids or alkaline salts thereof, sequestering agents or free-radical scavengers; mention may be made of sulphuric acid, phosphoric acid, sodium pyrophosphate or even dipicolinic acid, phosphonic acids or butyl hydroxytoluenes. Depending on the use envisaged, the composition according to the invention can also contain dyes and/or fragrances.

The aqueous solution according to the invention can also contain a dyestuff such as a dye, in particular a compound containing a monoazo function —N=N—, or a pigment sold in the form of a ready-to-use dispersion, in particular a pigment of the phthalocyanine family.

The subject of the invention is, in particular, a composition as defined above, in the form of an aqueous solution comprising from 0.0001% to 1% by weight of a dyestuff. The term dyestuff is understood to refer to any agent which is compatible with peracetic acid, and in particular those described in the European patent application EP 0,658,309 published on Jun. 21, 1995, and in particular the following compounds: Orange soleil [Sunburst orange] W2002 or Rouge vif [Bright red] W3002, sold by the company Wacker; Hostafine Blue B26 or Hostafine Green GN sold by the company Hoechst AG and dye E102.

The subject of the invention is also a composition as defined above also containing a corrosion inhibitor chosen from phosphoric acid salts and preferably from sodium dihydrogen phosphate and sodium hydrogen phosphate.

The concentration of corrosion inhibitor depends on that of a peracetic acid and of hydrogen peroxide; it is in particular between 0.01% and 10% by weight and preferably between 0.5% and 5% by weight.

The subject of the invention is in particular a composition as defined above, for which the weight ratio between the compound of formula (I) and peracetic acid is less than or equal to 0.2.

Depending on the recommended use, the composition according to the invention will be more or less concentrated with peracetic acid.

A composition as defined above intended to be diluted before use preferably comprises from 2% to 6% by weight of peracetic acid, from 10% to 20% by weight of hydrogen peroxide, from 10% to 20% by weight of acetic acid, from 0.01% to 0.3% by weight of at least one compound of formula (I) and, if desired, from 0.1% to 0.3% by weight of at least one nonionic surfactant.

A ready-to-use composition as defined above preferably comprises, depending on the use made thereof, from 0.0005% to 5% by weight of peracetic acid, from 0.001% to 10% by weight of hydrogen peroxide, from 0.001% to 20% by weight of acetic acid, from 0.0001% to 1% by weight of at least one compound of formula (I) and, if desired, from 0.0001% to 0.2% by weight of at least one compound of formula (II), such as, for example, a composition (A) which comprises from 0.0005% to 0.05% by weight of peracetic acid, from 0.01% to 0.30% by weight of acetic acid, from 0.3% to 5% of hydrogen peroxide, from 0.0005% to 0.01% by weight of at least one compound of formula (I) and from 0.0001% to 0.005% by weight of at least one compound of formula (II), or a composition (B) which comprises from 0.1% to 1% by weight of peracetic acid, from 4% to 10% by weight of hydrogen peroxide, from 1% to 20% by weight of acetic acid, from 0.01% to 1% by weight of at least one compound of formula (I) and, if desired, from 0.02% to 0.2% of at least one nonionic surfactant or alternatively a composition (B$_1$) which comprises from 0.25% to 0.75% by weight of peracetic acid, from 6% to 10% by weight of hydrogen peroxide, from 2% to 10% by weight of acetic acid, from 0.015% to 0.75% by weight of at least one compound of formula (I) and, if desired, up to 0.15% by weight of a nonionic surfactant.

The subject of the invention is, in particular, a composition in the form of an aqueous solution comprising from 0.001% to 3% by weight of peracetic acid, from 0.001% to 10% by weight of hydrogen peroxide, from 0.001% to 10% by weight of acetic acid, from 0.001% to 1% by weight of compound of formula (I), from 0.001% to 0.1% by weight of compound of formula (II), from 0.01% to 10% by weight of corrosion inhibitor and, if desired, from 0.001% to 1% by weight of stabilizer.

As an example of such a composition, there is composition (C) comprising from 0.05% to 0.1% by weight of peracetic acid, from 3% to 4% by weight of hydrogen peroxide, from 2% to 3% by weight of acetic acid, from 0.003% to 0.006% by weight of compound of formula (I), from 0.001% to 0.005% by weight of compound of formula (II), from 0.1% to 0.8% by weight of sodium dihydrogen phosphate, from 0.05% to 0.1% by weight of sodium pyrophosphate and, if desired, from 0.0001% to 0.05% by weight of a dyestuff.

Such ready-to-use compositions preferably have a (peracetic acid +acetic acid)/hydrogen peroxide weight ratio of less than 1.

The composition according to the invention is prepared according to methods known to those skilled in the art, in particular using solutions and surfactants that are commercially available or described in the literature. It is possible, for example, either to add the product of formula (I) to an aqueous solution comprising peracetic acid, hydrogen peroxide and acetic acid, or to add the tertiary amine corresponding to the product of formula (I) into the solution; in this case, the compound of formula (I) is prepared "in situ" by the action of hydrogen peroxide on the tertiary amine.

In another aspect of the present invention, its subject is the composition as defined above for the disinfection of hard surfaces. The term hard surfaces is understood to refer, for example, to floors, walls, the walls of containers, table tops and shelving, the surfaces of any material, container or equipment used, for example, in the food and agrifood industries or in activities for preparing, transforming and packaging food and drinks, in the bioindustries, the pharmaceutical industries, the cosmetics industries, clean rooms, greenhouses and growing or rearing premises, or alternatively in the field of health and hygiene; the compositions according to the invention are, in this case, used to disinfect hospital premises, medico-surgical equipment and dentistry equipment. The term hard surfaces is also understood to refer, for example, either to smooth flat surfaces or to concave surfaces with a smooth or granular appearance, or even to the surfaces of objects with complex shapes containing, in particular, cavities, such as pipes or catheters.

The surface to be treated can be made of any material and in particular of wood, glass, metal, for example of enamelled steel or of stainless steel, of ceramic, of organic polymer such as, for example, polyethylenes, polypropylenes, polycarbonates, polyamides, polyesters such as polyethylene terephthalates (PET), polyurethanes, fluoropolymers such as PTFE, PVDF or PFA, or of polyvinyl chlorides (PVC); it can also be a surface painted with a glycerophthalic, acrylic or vinylic paint.

In a preferred aspect of the present invention, the composition as defined above is used to clean containers used in the food industry and intended to come into contact with food products and in particular with milk or milk-based products.

In another preferred aspect, the composition as described above is used for the disinfection of bottles or any container intended to receive food liquids, for instance drinks such as, for example, mineral water, fruit juice and beer, in the bottling industry, and in particular in cleaning bottles made of polyethylene terephthalate (PET).

In another preferred aspect of the present invention, the ready-to-use composition as described above can be used to disinfect and descale the equipment used in all the stages of the dialysis line, in particular such as the water-treatment circuits for blood dialysis, and more particularly the recycling loop, the dialysis generators, the dialysers, the blood filters, the blood dialysers or the blood diafilters. The composition (B) as described above can be used in particular as described in European patent application EP 0,370,850.

In another preferred aspect of the present invention, the composition as defined above is used in hospital hygiene, in particular for disinfecting reusable medico-surgical equipment such as, for example, endoscopes. The composition (C) as described above is particularly suitable for such a use.

On account of their stability and their harmlessness, the composition as defined above can also be used in a non-hospital environment, in particular by medical practitioners with a private practice, for cleaning and disinfecting their reusable consultation equipment such as, for example, dentistry equipment or acupuncture needles. The compositions (A) or (C) as described above are also particularly suitable for such a use.

The composition $B_1$, as defined above, is particularly suitable for disinfecting medico-surgical devices such as, for example, endoscopes when the disinfection is achieved in machines. In this case, composition $B_1$ is diluted in water between 1/3 and 1/10, and more particularly at the fifth.

In a final preferred aspect of the present invention, the composition as defined above can be used for the treatment of unseasoned wood and in particular unseasoned wood which has become blue-stained by moulds.

Depending on the use made thereof, the composition according to the invention is used manually, semi-automatically or automatically, for example by spraying, dipping, dusting or recycling in the equipment whose inner walls are to be disinfected.

In a final aspect of the present invention, the dilute solution or composition is absorbed onto a porous material such as a sponge, paper or tissue, in order to form a ready-to-use formulation on a solid support, for example such as a wipe.

DETAILED DESCRIPTION OF THE INVENTION

The examples which follow illustrate the invention without, however, limiting it.

A—Preparation of the Compositions According to the Invention

The following compositions were prepared by adding Genapol® 2908D (II) and either cocodimethylamine oxide (Ia) or tetradecyldimethylamine oxide (Ib), which are sold under the brand name Aromox®, to a commercial solution of peracetic acid.

| Composition | PAA % by weight | $H_2O_2$ % by weight | AA % by weight | Compound of formula (I) % by weight | Compound of formula (II) % by weight |
|---|---|---|---|---|---|
| 1 | 5.5 | 14.5 | 16.5 | (Ia) 0.30 | 0.24 |
| 2 | 5.5 | 14.5 | 16.5 | (Ia) 0.20 | 0.24 |
| 3 | 5.5 | 14.5 | 16.5 | (Ia) 0 10 | 0.24 |
| 4 | 5.5 | 14.5 | 16.5 | (Ia) 0.05 | 0.24 |

-continued

| Composition | PAA % by weight | H₂O₂ % by weight | AA % by weight | Compound of formula (I) % by weight | Compound of formula (II) % by weight |
|---|---|---|---|---|---|
| 5 | 5.5 | 14.5 | 16.5 | (Ia) 0.02 | 0.24 |
| 6 | 5.0 | 14.5 | 16.5 | (Ia) 0.30 | 0.24 |

Starting with compositions 1 to 6 according to the invention, the following compositions, which are also subjects of the present invention, were prepared by dilution in water:

| Composition | PAA % by weight | (I) % by weight | pH |
|---|---|---|---|
| 1A | 0.050 | 0.0027 | 3.15 |
| 1B | 0.035 | 0.0019 | 3.29 |
| 1C | 0.020 | 0.0011 | 3.52 |
| 2A | 0.070 | 0.0925 | 2.99 |
| 2B | 0.055 | 0.0020 | 3.12 |
| 2C | 0.040 | 0.0014 | 3.26 |
| 3A | 0.090 | 0.0014 | 2.98 |
| 3B | 0.080 | 0.0011 | 3.11 |
| 3C | 0.040 | 0.0007 | 3.30 |
| 4A | 0.200 | 0.0017 | 2.59 |
| 4B | 0.170 | 9.0015 | 2.69 |
| 4C | 0.140 | 0.0012 | 2.77 |
| 4D | 0.100 | 0.0009 | 2.93 |
| 5A | 0.260 | 0.0012 | 2.45 |
| 5B | 0.240 | 0.0011 | 2.47 |
| 5C | 0.220 | 0.0019 | 2.50 |
| 5D | 0.200 | 0.0099 | 2.56 |
| 6A | 0.055 | 0.003 | 3.20 |

With the exception of solution 6A for which the compound of formula (I) is the compound (Ib), all the other solutions contain the compound (Ia).

B—Analysis of the Fungicidal Properties of the Compositions According to the Invention The fungicidal activity of the compositions according to the invention was evaluated on Candida parapsilosis according to AFNOR procedure NFT 72 201 (contact time: 15 minutes; temperature 20° C.). The following logarithmic reductions are obtained:

| Composition | Log. Reduction |
|---|---|
| 1A | 6.9 |
| 1B | 6.7 |
| 2A | 6.2 |
| 2B | 6.2 |
| 2C | 5.4 |
| 3A | 6.3 |
| 4A | >7 |
| 4B | >7 |
| 4C | >7 |
| 5A | >7 |
| 5B | >7 |
| 5C | >7 |
| 5D | >7 |
| 6A | >7 |

C—Comparative Study

The fungicidal activity was evaluated on Candida parapsilosis according to AFNOR standard NFT 72201 (contact time 15 minutes; temperature 20° C.) of the following aqueous solutions:

| Solution | PAA % W/W | Acetic acid % W/W | Amine oxide of formula (Ia) % W/W | pH |
|---|---|---|---|---|
| A | 0 | 2.5 | 0.003 | 2.62 |
| B | 0.29 | 0.9 | 0 | 2.25 |
| C | 0 | 2.5 | 0 | 2.62 |
| D | 0 | 0 | 0.008 | 6.67 |

The following logarithmic reductions are obtained:

| Solution | Log. Reduction |
|---|---|
| A | 5.5 |
| B | 4.6 |
| C | 0 |
| D | 0 |

The results show that:

in order to obtain a logarithmic reduction of 4.6, a concentration of PAA, in a solution free of amine oxide, of 0.29% (solution B) is needed;

in order to obtain a logarithmic reduction of 5.5, a concentration of amine oxide, in a solution free of peracetic acid, of 0.003% (solution A) in acidic medium is needed;

with a solution containing altogether half as much peracetic acid (0.14%) and 2.5 times less amine oxide (0.0012%), a logarithmic reduction of greater than 7 is obtained, i.e. a fungicidal activity about 100 times as large; (solution 4C).

The excellent results observed are thus due to the synergism induced by the presence of peracetic acid and an amine oxide in the same composition.

What is claimed is:

1. A composition for disinfecting medico-surgical equipment, comprising:
   a) from 0.0005% to 5% by weight of peracetic acid,
   b) from 0.01% to 3% by weight of acetic acid,
   c) from 0.3% to 10% by weight of hydrogen peroxide,
   d) from 0.0001% to 1% by weight of at least one compound of formula (I)

$$(R_1)(R_2)(R_3)N \rightarrow O \qquad (I)$$

in which, either $R_1$ represents a linear or branched, cyclic or acyclic radical containing from 1 to 40 carbon atoms and optionally from 1 to 6 hetero atoms selected from the group consisting of oxygen, sulphur and nitrogen, and $R_2$ and $R_3$, which may be identical or different, represent a linear or branched alkyl radical containing from 1 to 4 carbon atoms or a linear or branched hydroxyalkyl radical containing from 1 to 4 carbon atoms; or $R_1$ and $R_2$ represent, together with the nitrogen atom to which they are attached, a saturated or unsaturated, substituted or unsubstituted heterocycle containing from 5 to 8 carbon atoms and from 1 to 4 hetero atoms selected from the group consisting of oxygen, nitrogen and sulphur, and $R_3$ represents a linear or branched alkyl radical containing from 1 to 4 carbon atoms or a linear or branched hydroxyalkyl radical containing from 1 to 4 carbon atoms, e) optionally from 0.0001% to 0.2% by weight of at least one non-ionic surfactant, and where in f) the weight ratio between the compound of formula (I) and the peracetic acid is less than or equal to 1, g) the weight ratio between the non-ionic surfactant and the peracetic acid is less than or equal to 0.2, and h) the weight ratio of peracetic acid+acetic acid to hydrogen peroxide is less than 1, provided that the non-ionic surfactant which is optionally comprised within said composition is not a compound having the formula (III)

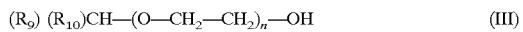

$$(R_9)(R_{10})CH\text{—}(O\text{—}CH_2\text{—}CH_2)_n\text{—}OH \quad\quad (III)$$

in which $R_9$ and $R_{10}$ are each either hydrogen or linear, or branched alkyl wherein $R_9$ plus $R_{10}$ has a total of from 7 to 22 carbon atoms, and n is selected in the range of 1 to 15, wherein the number ratio of carbon atoms in $R_9$ plus $R_{10}$: n is greater than or equal to 3:1, and provided that the non-ionic surfactant is not a dinonyl phenolethoxylate of EO from 4 to 8.

2. The composition according to claim 1, wherein the non-ionic surfactant comprises at least one compound of formula (II)

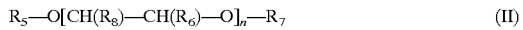

$$R_5\text{—}O[CH(R_8)\text{—}CH(R_6)\text{—}O]_n\text{—}R_7 \quad\quad (II)$$

in which $R_5$ represents a linear or branched, saturated or unsaturated aliphatic radical containing from 5 to 31 carbon atoms; $R_6$ and $R_8$ each represent a hydrogen atom, a methyl radical or an ethyl radical, wherein at least one of the two radicals $R_6$ or $R_8$ represents a hydrogen atom, $R_7$ represents a hydrogen atom or a linear or branched alkyl radical containing from 1 to 4 carbon atoms, or a benzyl radical, n represents a number between 1 and 50; or the group [CH($R_8$)—CH($R_6$)—O]$_n$ represents a chain consisting approximately of between 5 and 8 —(CH$_2$—CH$_2$—O)— structural units and approximately of between 1 and 5 —(CH$_2$—CH(CH$_3$)—O)— structural units, said structural units being distributed in said chain in a random or block manner; provided that the at least one compound of formula (II) is not a compound of formula (III).

3. The composition according to claim 2, wherein:
    a) the peracetic acid is from 0.005% to 0.5% by weight;
    b) the acetic acid is from 0.01% to 0.30% by weight;
    c) the hydrogen peroxide is from 0.3% to 5% by weight;
    d) the at least one compound of formula (I) is from 0.0005% to 0.01% by weight; and
    e) the at least one compound of formula (II) is from 0.0001% to 0.005% by weight.

4. The composition according to claim 2, wherein:
    a) the peracetic acid is from 0.05% to 0.10% by weight;
    b) the acetic acid is from 2% to 3% by weight;
    c) the hydrogen peroxide is from 3% to 4% by weight;
    d) the compound of formula (I) is from 0.003% to 0.006% by weight;
    e) the compound of formula (II) is from 0.001% to 0.005% by weight;

said composition further comprising:
    f) from 0.1% to 0.8% by weight of sodium dihydrogen phosphate; and
    g) from 0.05% to 0.1% by weight of sodium pyrophosphate.

5. A method of disinfecting a medico-surgical equipment, which comprises adding an effective amount of the disinfecting composition of claim 1 to the medico-surgical equipment.

6. The method according to claim 5, wherein the medico-surgical equipment is an endoscope.

7. A method of disinfecting a medico-surgical equipment, which comprises adding an effective amount of the disinfecting composition of claim 2 to the medico-surgical equipment.

8. The method according to claim 7, wherein the medico-surgical equipment is an endoscope.

9. A method of disinfecting a medico-surgical equipment, which comprises adding an effective amount of the disinfecting composition of claim 3 to the medico-surgical equipment.

10. The method according to claim 9, wherein the medico-surgical equipment is an endoscope.

11. A method of disinfecting a medico-surgical equipment, which comprises adding an effective amount of the disinfecting composition of claim 4 to the medico-surgical equipment.

12. The method according to claim 11, wherein the medico-surgical equipment is an endoscope.

* * * * *

UNITED STATES PATENT AND TRADEMARK OFFICE
CERTIFICATE OF CORRECTION

PATENT NO. : 6,444,230 B1
DATED : September 3, 2002
INVENTOR(S) : Catherine Hamon Godin et al.

It is certified that error appears in the above-identified patent and that said Letters Patent is hereby corrected as shown below:

<u>Title page,</u>
Item [12], amend to read as follows: -- [12] Hamon Godin et al. --.

Signed and Sealed this

Thirty-first Day of December, 2002

JAMES E. ROGAN
*Director of the United States Patent and Trademark Office*